United States Patent
Gibson

(10) Patent No.: US 11,166,423 B2
(45) Date of Patent: Nov. 9, 2021

(54) LETTUCE VARIETY 'PRO 1278'

(71) Applicant: PROGENY ADVANCED GENETICS, Salinas, CA (US)

(72) Inventor: George Darryn Gibson, Prunedale, CA (US)

(73) Assignee: Syngenta Crop Protection AG, Basel (CH)

( * ) Notice: Subject to any disclaimer, the term of this patent is extended or adjusted under 35 U.S.C. 154(b) by 81 days.

(21) Appl. No.: 16/736,432

(22) Filed: Jan. 7, 2020

(65) Prior Publication Data

US 2020/0221661 A1 Jul. 16, 2020

Related U.S. Application Data

(60) Provisional application No. 62/791,518, filed on Jan. 11, 2019.

(51) Int. Cl.
*A01H 6/14* (2018.01)
*A01H 5/12* (2018.01)

(52) U.S. Cl.
CPC ............ *A01H 6/1472* (2018.05); *A01H 5/12* (2013.01)

(58) Field of Classification Search
None
See application file for complete search history.

(56) References Cited

U.S. PATENT DOCUMENTS 9,700,012 B2 * 7/2017 Gibson .................... A01H 5/12
2017/0258030 A1 * 9/2017 Gibson ............... A01H 6/1472

OTHER PUBLICATIONS

Liu et al. (1999). "First report of tomato bushy stunt virus isolated from lettuce," Plant Dis. 83:301.
Nagata (1992). "Clip and Wash Method of Emasculation for Lettuce," Hortscience 27(8):907-908.
Obermeier et al. (2001). "Characterization of Distinct Tombusviruses that Cause Diseases of Lettuce and Tomato in the Western United States," Phytopathology. 91(8):797-806.
Ryder et al. (1974). "Mist depollination of lettuce flowers," Hortscience 9:584.
US Plant Variety Protection Certificate No. 200200013, Issued Dec. 12, 2005, Variety Name Big Star, Crop Name Lettuce, Applicant Central Valley Seeds, Inc., 34 pages.
US Plant Variety Protection Certificate No. 200500262, Issued Feb. 5, 2008, Variety Name Bergam's Green, Crop Name Lettuce, Applicant Enza Zaden Beheer B.V., 54 pages.

* cited by examiner

*Primary Examiner* — Ashley K Buran
(74) *Attorney, Agent, or Firm* — Karen A. Magri

(57) ABSTRACT

A new lettuce variety designated 'PRO 1278' is described. 'PRO 1278' is a green leaf lettuce variety exhibiting stability and uniformity.

11 Claims, No Drawings

LETTUCE VARIETY 'PRO 1278'

CROSS-REFERENCE TO RELATED APPLICATION

This application claims the benefit of U.S. Provisional Application No. 62/791,518, filed Jan. 11, 2019, which is hereby incorporated by reference in its entirety.

FIELD

This invention relates to the field of plant breeding. In particular, this invention relates to new lettuce, *Lactuca sativa*, variety 'PRO 1278'.

BACKGROUND

Lettuce is an increasingly popular crop. Worldwide lettuce consumption continues to increase. As a result of this demand, there is a continued need for new lettuce varieties. In particular, there is a need for improved green leaf lettuce varieties that exhibit improved growth habits, bolting and tip burn tolerance, and disease resistance.

SUMMARY

In order to meet these needs, the present invention is directed to an improved green leaf lettuce variety with a medium green color and open growth habit that produces a high number of uniform leaves, and has improved tolerance to bolting and tip burn as well as resistance to Tomato Bushy Stunt Virus (tombusvirus, TBSV).

In particular, the present invention is directed to lettuce, *Lactuca sativa*, seed designated as 'PRO 1278' having ATCC Accession Number PTA-126609. The present invention is further directed to lettuce, *Lactuca sativa*, plants and the lettuce heads isolated therefrom produced by growing 'PRO 1278' lettuce seed.

The present invention is further directed to a *Lactuca sativa* plant and the lettuce head isolated therefrom having all the physiological and morphological characteristics of a *Lactuca sativa* plant produced by growing 'PRO 1278' lettuce seed having ATCC Accession Number PTA-126609. The present invention is further directed to an F1 hybrid lettuce, *Lactuca sativa*, seed, plants grown from the seed and a head isolated therefrom having 'PRO 1278' as a parent wherein 'PRO 1278' is grown from 'PRO 1278' lettuce seed having ATCC Accession Number PTA-126609.

The present invention is further directed to pollen and ovules isolated from 'PRO 1278' lettuce plants. The present invention is further directed to tissue culture of 'PRO 1278' lettuce plants.

The present invention is further directed to a method of selecting lettuce plants comprising: a) growing 'PRO 1278' lettuce plants wherein the 'PRO 1278' plants are grown from lettuce seed having ATCC Accession Number PTA-126609, and b) selecting a plant from step a). The present invention is further directed to lettuce plants and seeds produced by the lettuce plants wherein the lettuce plants are isolated by the selection method of the invention.

The present invention is further directed to a method of breeding lettuce plants comprising crossing a lettuce plant with a plant grown from 'PRO 1278' lettuce seed having ATCC Accession Number PTA-126609. The present invention is further directed to lettuce plants, heads from the lettuce plants, and seeds produced therefrom where the lettuce plant is isolated by the breeding method of the invention.

DETAILED DESCRIPTION

In order to more clearly understand the invention, the following definitions are provided:

Green Leaf Lettuce: Green leaf lettuce is *Lactuca sativa* L. The plant develops in an upright open growing habit with medium textured leaves. The leaves are typically somewhat savoyed, while the shape can vary by variety. Leaf margins are often undulated or frilled. Other leaves range in color from light green to dark green with a minimal midrib. Inner heart leaves are typically smaller and lighter green in color.

Core Length: Core length is the length of the internal lettuce stem. Core length is measured from the base of the cut head to the tip of the core.

Core Diameter: Core diameter is the diameter of the lettuce stem at the base of the cut head.

Green Leaf Heart: Green leaf heart is the densest part of the green leaf plant often yellow and light green in color and of succulent texture. The heart is generally enclosed by two to three outer darker green leaves.

Heart Length: Heart length is the length of the vertically sliced lettuce plant as measured from the base of the cut stem to the top leaf margin of the longest outermost leaf that encloses the green leaf heart.

Head Length to Core Length Ratio: The ratio of the head length to core length is indicative of the percentage of useable product produced by the lettuce plant.

Plant Diameter: The plant diameter is a measurement across the top of the lettuce plant at its widest point. The measurement of frame diameter is taken from the outer most leaf tip horizontally to the outer most leaf tip.

Head Weight: Head weight is the weight of the marketable lettuce plant, cut and trimmed to market specifications.

Rogueing: Rogueing is the process in lettuce seed production where undesired plants are removed from a variety. The plants are removed because they differ physically from the general desired expressed characteristics of the variety. The differences can be related to size, color, maturity, leaf texture, leaf margins, growth habit, or any other characteristic that distinguishes the plant.

Market Stage: Market stage is the stage when a lettuce plant is ready for commercial lettuce harvest. In the case of a green leaf lettuce variety, a green leaf plant is at a marketable state when the heart has some density and the head has reached an adequate size and weight.

Tomato Bushy Stunt Virus (TBSV): Lettuce dieback was first observed in California in the mid-1980s, and reports of the disease have increased over the last 10 years. Complete crop losses have occurred in fields of green leaf lettuce, and no commercial green leaf cultivar has been shown to be resistant to the disease. In the U.S., green leaf is a rapidly growing market segment, having increased 68% over the last five years (USDA, 2002). The disease has occurred in commercial fields of some leaf lettuce cultivars; however, symptoms have never been observed on any modern crisphead (iceberg) cultivars. Lettuce dieback is caused by several related tombusviruses including TBSV and Lettuce Necrotic Stunt Virus (LNSV) (Liu et al., 1999; Obermeier et al., 2001). These are soilborne, highly stable, and mechanically transmitted, and have no known vector. The conditions affecting symptom development remain poorly understood. The disease is frequently observed in low-lying areas of fields with a prior history of flooding, suggesting that the virus may be carried in river water and/or that disease symptoms may be associated with increased root stresses such as those presented by excess moisture. No effective cultural or chemical control methods have yet been identified.

Resistance to TBSV refers to a level of resistance in a lettuce variety as measured by visual symptoms. Resistance is deemed present when symptoms are not present in at least 95% of a lettuce variety when exposed to TBSV.

Taking into account these definitions, the present invention is directed to seeds of the lettuce variety 'PRO 1278', plants produced by growing 'PRO 1278' lettuce seeds, head isolated or harvested from the plants, one or more plants selected from a collection of 'PRO 1278' plants and seeds derived or produced therefrom; plants produced by crossing a lettuce plant with a 'PRO 1278' lettuce plant and seeds derived or produced therefrom.

Origin and Breeding History of the Variety 'PRO 1278'

'PRO 1278': 'PRO 1278' is an open growing green leaf variety that produces a high number of leaves that are uniform in size and shape. This variety is distinct and unique to all other green leaf lettuce varieties due to its combined disease and physiological resistances. 'PRO 1278' has a unique and valuable resistance, as it is resistant to TBSV, a very problematic disease found throughout the Salinas and Imperial valleys of California. In addition to this disease resistance, 'PRO 1278' is also resistant to the physiological problems associated with lettuce production in areas of higher temperatures such as internal tip burn and fringe burn, and has an improved resistance to bolting.

'PRO 1278' is a green leaf lettuce variety developed from a hand pollinated cross of two Progeny Advanced Genetics proprietary breeding lines. The two parental varieties were selected for their specific disease and physiological resistances, their respective adaptations, and their leaf shape.

The cross was made in Year 1, and through the single seed descent breeding method, we have developed a slightly savoyed and slow to medium growing green leaf variety with a high leaf count, good weight, a desired rectangular leaf shape, and a low core. 'PRO 1278' is resistant to TBSV. Through extensive field trialing and screenings 'PRO 1278' has demonstrated resistance to TBSV, tip burn and fringe burn, while being slower bolting than other TBSV-resistant green leaf varieties.

In a Year 1 Progeny Advanced Genetics research greenhouse a cross was made of two Progeny green leaf breeding lines. The parent lines were selected for their resistances, their shape and structure, and their adaptability. The F1 seed was harvested in the fall of Year 1 and designated as ONE.

In Year 2, 20 F1 seeds of ONE were planted in Progeny's research green house facility in Watsonville, Calif., indicated by Progeny research line number TWO. The F1 plants were allowed to self pollinate, and the F2 seed was harvested in bulk. The seed was immediately cleaned, processed, blended, and prepared for planting.

One hundred random F2 seeds of line number TWO were again planted in the Progeny Advanced Genetics research green house facility and redesignated as THREE. Segregation amongst the F2 population was noted and all plants were allowed to self pollinate and produce seed. The F3 seed from each plant was harvested and packaged individually in the fall of Year 2. One seed from each package (plant) was removed and placed in one envelope and designated as FOUR, and planted again in the research greenhouse facility. The F3 plants were evaluated at multiple stages of maturity, where segregation for phenotype and maturity was again evident and noted, and all plants were allowed to self pollinate and produce seed. F4 seed from 100 individual plants was harvested, cleaned and packaged individually.

The 100 F4 lines, all from selected single F3 plants of the pedigree ONE, were processed in our California facility. A trial was prepared containing each of the 100 F4 individual lines of the designated pedigree, the parent varieties, and susceptible and resistant standard varieties as checks for the multiple diseases. The Progeny Advanced Genetics research trial was planted twice in the Salinas valley in the spring of Year 4 in fields known to be infected with TBSV. The trials were evaluated in the summer of Year 4. All F4 lines were evaluated based on phenotypic uniformity, improved leaf size and shape, improved weight, bolting resistance, and improved tolerances to tip burn and fringe burn when compared to the parent and check varieties. The F4 lines were also rated on their resistance to TBSV. After multiple evaluations of the trials, three F4 lines of this pedigree were selected as they out-performed the parent varieties, their sibs, and the majority of other lines in the trial for the designated traits. The three selected F4 lines, among them FOUR-4 B/S, were increased in a summer research and development seed production crop. The F5 seed was harvested in bulk in the fall of year 5. F5 seed from F4 line FOUR-4 B/S was designated as FIVE. The production block was rogued at multiple stages of maturity and designated as uniform and stable.

The three F5 lines of this pedigree, including line number FIVE, along with their parent lines and check varieties were evaluated in multiple trials in the lettuce production regions of California and Arizona. Multiple fields in the California trials were known to harbor TBSV. The F5 lines were screened for resistance to the diseases present, as well as tip burn and fringe burn. Yield traits such as weight, core length, leaf count, leaf size and leaf shape were also evaluated. FIVE continued to be resistant to TBSV while having a low core, and being free of the symptoms associated with tip and fringe burn. This line also rated higher than its sister lines for leaf size, leaf shape and leaf count.

Based on the trial data, and the disease resistance, seed from FIVE was again increased in a San Joaquin valley research and development seed production crop in a block containing roughly 1000 plants. The F7 seed was harvested.

An additional increase of the F7 seed was made in a Yuma Ariz. seed production field, under higher temperatures and more adverse weather conditions. During the rogueing process, less than 2% off-types were noted and multiple individual plant selections were made from which the F8 seed was harvested and processed individually, including a plant indicated as SIX. This plant was noted to be significantly slower bolting, and with a higher leaf count than the remaining population.

500 seeds from the F8 individual plant selection SIX were then planted in our in our San Joaquin valley research and development production field for evaluation and seed increase. This block was indicated as stake number SEVEN, and was rogued and multiple stages of maturity. The block was indicated as uniform and stable, and again significantly slower bolting than selected sister lines. The F9 bulk seed was harvested and trialed throughout the California and Arizona lettuce production areas for the next two seasons. This variety continued to be slower bolting and maintained a higher leaf count than its sister lines and competitive varieties on the market.

The F9 seed was increased again in a San Joaquin valley research and development field and consistently rogued and evaluated at multiple stages of maturity until harvest of the F10 seed. The variety was indicated to be uniform and stable without variants, and designated 'PRO 1278'

As evaluated in multiple seed production fields and commercial plantings, the F9 and F10 generations of seeds from the variety 'PRO 1278' have been uniform and stable without variants.

A. Variety Description Information

'PRO 1278' is a uniform and distinct variety of green leaf lettuce. The distinctness and utility of the variety are based on its resistance to Tomato Bushy Stunt Virus (TBSV), combined with its environmental adaptability, its leaf size, its leaf shape and its higher leaf count. 'PRO 1278' has numerous distinguishing characteristics as outlined in Table 1, below.

TABLE 1

| | |
|---|---|
| Plant Type: | Green Leaf |
| Seed: | |
| Seed Color: | Black |
| Light Dormancy: | No |
| Heat Dormancy: | Yes |
| Cotyledons: | |
| Shape of Cotyledons: | Intermediate |

TABLE 1-continued

| | |
|---|---|
| Shape of Fourth Leaf: | Spatulate |
| Length/Width Index of Fourth Leaf: | 16 |
| Apical Margin: | Moderately Dentate |
| Basal Margin: | Moderately Dentate |
| Undulation: | Medium |
| Green Color: | Medium |
| Anthocyanin: | Absent |
| Distribution: | None |
| Rolling: | Absent |
| Cupping: | Uncupped |
| Reflexing: | None |
| Mature Leaves: | |
| Margin: | |
| Incision Depth (Deepest Penetration of the Margin): | Moderate |
| Indentation (Finest Division of the Margin): | Deeply Dentate |
| Undulation of the Apical Margin: | Moderate |
| Green Color: | Medium |
| Anthocyanin: | |
| Distribution: | None |
| Size: | Large |
| Glossiness: | Moderate |
| Blistering: | Slight |
| Leaf Thickness: | Thick |
| Trichomes: | Absent |

B. Comparison to Most Similar Varieties

'PRO 1278' most closely resembles the lettuce variety 'Bergam's Green', however as indicated in Table 2, below, 'PRO 1278 is unique and distinct from 'Bergam's Green' by the following traits: PRO 1278 has a narrower leaf margin than 'Bergam's Green'. PRO 1278 has a shorter core than 'Bergam's Green'. PRO 1278 has a higher leaf count than 'Bergam's Green'. Table 2 provides averages from three trials in which lettuce variety 'PRO 1278' (20 plants per trial; 60 plants over all three trials) and lettuce variety 'Bergam's Green' (20 plants per trial; 60 plants over all three trials) were compared. This data is all statistically significant at a minimum of 95% confidence level and presented in detail in Tables 4-6 of Example 2.

TABLE 2

| Characteristic | PRO 1278 | Bergam's Green |
|---|---|---|
| Leaf Margin Width | 144.11 mm | 175.83 mm |
| Core Length | 39.22 mm | 54.66 mm |
| Leaf Count | 32.6 | 28.62 |

'PRO 1278' also resembles the green leaf variety 'Big Star', however 'PRO 1278' is distinct from 'Big Star' by the following traits: PRO 1278 has a longer core length than 'Big Star'. PRO 1278 has a higher leaf count than 'Big Star'. PRO 1278 is resistant to TBSV where as 'Big Star' is susceptible to TBSV. Table 3, below, provides averages from three trials in which lettuce variety 'PRO 1278' (20 plants per trial; 60 plants over all three trials) and lettuce variety 'Big Star' (20 plants per trial; 60 plants over all three trials) were compared. This data is all statistically significant at a minimum of 95% confidence level and presented in detail in Tables 7-10 of Example 2.

TABLE 3

| Characteristic | PRO 1278 | Big Star |
|---|---|---|
| Core Length | 39.22 mm | 26.28 mm |
| Leaf Count | 32.6 | 27.87 |
| Mortality from TBSV | 0% | 63.33% |

Breeding and Selection

The present invention is further directed to the use of 'PRO 1278' lettuce in breeding and selection of new varieties.

A. Breeding

In lettuce breeding, lines are selected for certain desired appropriate characteristics. For example, one line may be selected for bolt tolerance in the fall growing conditions of the desert production locations of California and Arizona, or for resistance to viruses such as TBSV. Another line may be selected for the size, color and texture of the lettuce head. Crosses are made, for example, to produce a medium to light green, tip burn-resistant green leaf lettuce with improved texture and size for spring and summer harvest in the Salinas valley of California.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self pollinating possibilities, is very tedious and time consuming when a large number of crosses are to be made. The breeders have therefore adapted a well-documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 3 weeks after pollination, seeds are harvested when the involucre have matured. The seeds are eventually sown, and the selfed or maternal seedlings or plants are identified if markers such as leaf color or leaf margins are present. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for outcrossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908. Both references are hereby incorporated by reference in their entirety for the purpose of providing details on the techniques well known in the art.

B. Selection

In addition to crossing, selection may be used to identify and isolate new lettuce lines. In lettuce selection, lettuce seeds are planted, the plants are grown, and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally-selected line. Selection work is continued over multiple generations to increase the uniformity of the new line.

Deposit Information

Applicants have made available to the public without restriction a deposit of at least 625 seeds of lettuce variety 'PRO 1278' with the American Type Culture Collection (ATCC), P.O. Box 1549, MANASSAS, Va. 20108 USA, with a deposit on Jan. 14, 2020 which has been assigned ATCC number PTA-126609.

The deposit will be maintained in the ATCC depository, which is a public depository, for a period of 30 years, or 5 years after the most recent request, or for the effective life of the patent, whichever is longer, and will be replaced if a deposit becomes nonviable during that period.

This invention will be better understood by reference to the following non-limiting Examples.

EXAMPLES

Example 1: General Trialing Method

The following steps illustrate the general trialing method of the invention.

I. Set Up
1. A trial is set up to compare one or more lines. Parental lines and related varieties are identified.
2. Primary slots are identified.
3. Accession lines are located and purchased/obtained from seed dealers or growers.
4. All varieties are assigned a number to maintain integrity and anonymity.
5. Trials are set up in with all necessary varieties. Variety arrangement for trial is diagramed.

II. Planting
Commercial plantings are located by contacting commercial growers during the planting slot recommended for the variety.
2. A field is located during commercial planting and the necessary rows and area is marked off.
3. Varieties are planted according to a diagram, generally in 100 foot ranges.
4. All varieties are planted in same manner to mimic the planting of the commercial variety as closely as possible.
5. A trial map is drawn diagramming the trial, the trial location in the field, and directions to the field.

III. Maintenance
1. All tested varieties are treated identically. Plants are watered, fertilized, and treated to control pests in the same manner as other lettuce plants in the commercial field.
2. The trial is thinned to separate the plants for optimum growth.

IV. Evaluation
1. Evaluations are done as near to the time of the commercial harvest as possible.
2. The evaluation is conducted "blindly". The evaluator(s) do not have the key to the trial at the time of evaluation.
3. 24 heads of each variety are evaluated.

a. The frame diameters of 24 random plants are measured to the nearest cm.
b. 24 mature plants of each variety are cut to the cap leaf.
c. The following measurements are then conducted and recorded:
  1. Each plant is weighed to the nearest gram.
  2. The core diameter of each head is measured to the nearest mm.
  3. The heads are then sliced in to halves, discarding 1 half
  4. The core lengths (from the cut stem to the core tip) are measured to the nearest mm.
  5. The plant length (from the cut stem to the cap leaf) is measured to the nearest mm.
  6. The plant diameter (at its widest point) is measured to the nearest mm.
  7. The heart length is measured to the nearest mm.
  8. The ideal maturity or harvest date is then estimated based on the solidity of the plant, the core length and any other physiological characteristics present.
  9. The leaf color is documented using the Munsell Color Charts for Plant Tissue.
e. From these measurements, an Excel program is used to calculate the averages, the standard deviations and the T-Tests for the compared varieties.

Example 2: Comparative Analysis

Following the procedures of Example 1, 'PRO 1278' green leaf lettuce was compared to its parent and standard varieties. Comparative data was obtained and analyzed for the different green leaf lettuce lines. Core length, leaf count, leaf size, leaf shape, and head weight were compared.

'PRO 1278' is a uniform and distinct green leaf lettuce variety with a medium green color and a higher number of leaves that are uniform in size and shape. This variety has a slower growth rate and forms a medium sized plant with excellent pliability, and has a higher leaf count.

The most distinguishing characteristics of 'PRO 1278' are its unique resistance, combined with improved adaptability and multiple end uses. 'PRO 1278' is resistant to the Tombusvirus known as TBSV, and is further distinguished from other TBSV resistant varieties due to its improved resistance to bolting, and high number of leaves that are uniform in size and shape. As compared to other TBSV resistant green leaf varieties, 'PRO 1278' most closely resembles the lettuce variety 'Bergam's Green'. Tables 4-6 below show results of a first trial (Table 4), a second trial (Table 5), and a third trial (Table 6) that compare the leaf margin width, the core length, and the leaf count of 20 plants of the lettuce variety 'PRO 1278' with those of 20 plants of lettuce variety 'Bergam's Green' ("Bergam's"). As shown in Tables 4-6, 'PRO 1278' has a narrower leaf margin, a shorter core length, and a higher leaf count than 'Bergam's Green' (data all statistically significant at a minimum of 95% confidence level).

TABLE 4

| | Leaf Margin Width (mm) | | Core Length (mm) | | Leaf Count | |
| --- | --- | --- | --- | --- | --- | --- |
| | PRO 1278 | Bergam's | PRO 1278 | Bergam's | PRO 1278 | Bergam's |
| Average | 145.67 | 175.17 | 42.17 | 68.00 | 34.10 | 29.47 |
| Standard Deviation | 4.69 | 7.25 | 2.52 | 4.84 | 0.96 | 1.01 |
| t-test | 2.94375E−26 | | 1.3838E−33 | | 1.08025E−25 | |
| Probability | 100.00 | | 100.00 | | 100.00 | |
| % Difference | 16.8 | | 38.0 | | −15.7 | |
| Confidence Interval | 0.041 | 0.087 | 0.041 | 0.087 | 0.041 | 0.087 |

TABLE 5

| | Leaf Margin Width (mm) | | Core Length (mm) | | Leaf Count | |
|---|---|---|---|---|---|---|
| | PRO 1278 | Bergam's | PRO 1278 | Bergam's | PRO 1278 | Bergam's |
| Average | 142.67 | 177.17 | 37.83 | 51.83 | 32.00 | 27.93 |
| Standard Deviation | 5.68 | 3.87 | 5.83 | 3.82 | 1.31 | 1.55 |
| t-test | 5.95E−35 | | 7.96E−16 | | 9.45E−16 | |
| Probability | 100.00 | | 100.00 | | 100.00 | |
| % Difference | 19.5 | | 27.0 | | −14.6 | |
| Confidence Interval | 0.054 | 0.063 | 0.054 | 0.063 | 0.054 | 0.063 |

TABLE 6

| | Leaf Margin Width (mm) | | Core Length (mm) | | Leaf Count | |
|---|---|---|---|---|---|---|
| | PRO 1278 | Bergam's | PRO 1278 | Bergam's | PRO 1278 | Bergam's |
| Average | 144.00 | 175.17 | 37.67 | 44.17 | 31.70 | 28.47 |
| Standard Deviation | 5.15E+00 | 3.59E+00 | 4.50E+00 | 4.37E+00 | 1.15E+00 | 1.14E+00 |
| t-test | 1.09E−34 | | 4.63E−07 | | 9.43E−16 | |
| Probability | 100.00 | | 100.00 | | 100.00 | |
| % Difference | 17.8 | | 14.7 | | −11.4 | |
| Confidence Interval | 0.042 | 0.081 | 0.042 | 0.081 | 0.042 | 0.081 |

Based on plant type and adaptability, 'PRO 1278' most closely resembles the green leaf variety 'Big Star', but is most notably distinct by its resistance to TBSV. Tables 7-9 below show results of a first trial (Table 7), a second trial (Table 8), and a third trial (Table 9) that compare the core length, and the leaf count of 20 plants of the lettuce variety 'PRO 1278' with those of 20 plants of lettuce variety 'Big Star'. As shown in Tables 7-9, 'PRO 1278' has a longer core length and a higher leaf count than 'Big Star' (data all statistically significant at a minimum of 95% confidence level).

TABLE 7

| | Core Length (mm) | | Leaf Count | |
|---|---|---|---|---|
| | PRO 1278 | Big Star | PRO 1278 | Big Star |
| Average | 42.17 | 26.17 | 34.10 | 27.10 |
| Standard Deviation | 2.52 | 5.03 | 0.96 | 1.21 |
| t-test | 2.20811E−22 | | 1.50661E−32 | |
| Probability | 100.00 | | 100.00 | |
| % Difference | −61.1 | | −25.8 | |
| Confidence Interval | 0.041 | 0.087 | 0.041 | 0.087 |

TABLE 8

| | Core Length (mm) | | Leaf Count | |
|---|---|---|---|---|
| | PRO 1278 | Big Star | PRO 1278 | Big Star |
| Average | 37.83 | 25.00 | 32.00 | 27.90 |
| Standard Deviation | 5.83 | 4.35 | 1.31 | 1.71 |
| t-test | 1.08E−13 | | 6.61E−15 | |
| Probability | 100.00 | | 100.00 | |
| % Difference | −51.3 | | −14.7 | |
| Confidence Interval | 0.054 | 0.063 | 0.054 | 0.063 |

TABLE 9

| | Core Length (mm) | | Leaf Count | |
|---|---|---|---|---|
| | PRO 1278 | Big Star | PRO 1278 | Big Star |
| Average | 37.67 | 27.67 | 31.70 | 28.60 |
| Standard Deviation | 4.50E+00 | 4.50E+00 | 1.15E+00 | 1.75E+00 |
| t-test | 5.85E−12 | | 4.20E−11 | |
| Probability | 100.00 | | 100.00 | |
| % Difference | −36.1 | | −10.8 | |
| Confidence Interval | 0.042 | 0.081 | 0.042 | 0.081 |

Resistance was determined by growing the test variety, 'PRO 1278', against a known susceptible variety, 'Big Star', in fields where TBSV was present. The test plots were made as equivalent as possible using standard field plotting techniques and resistance was defined by visible infection. Infected plants can be severely stunted and mature, diseased plants may only reach 6 to 8 inches in height. The outermost leaves are extensively yellowed. The younger, inner leaves often remain dark green in color, but can be rough and leathery in texture. In some cases, the older leaves develop necrotic spotting that can turn into extensive areas of brown, dead tissue. There is no partial infection to provide relative scoring. The plants are either infected and scored with a '1' and die, or not infected and scored with a '0'. Table 10 below shows results of a first trial, a second trial, and a third trial that compare TBSV resistance of 20 plants of the lettuce variety 'PRO 1278' with that of 20 plants of lettuce variety 'Big Star'. The results clearly show that 'PRO 1278' is resistant to TBSV (data all statistically significant at a minimum of 95% confidence level).

TABLE 10

| | Trial 1 | | Trial 2 | | Trial 3 | |
|---|---|---|---|---|---|---|
| | PRO 1278 | Big Star | PRO 1278 | Big Star | PRO 1278 | Big Star |
| Average | 0 | 0.63 | 0 | 0.66 | 0 | 0.6 |
| Standard Deviation | 0 | 0.49 | 0 | 0.47 | 0 | 0.49 |
| t-test | 2.17206E−09 | | 2.7042E−10 | | 1.3966E−08 | |
| Probability | 100.00 | | 100.00 | | 100.00 | |
| % Mortality | 0.0 | 63.3 | 0.0 | 66.7 | 0.0 | 60.0 |

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. Lettuce seed designated as 'PRO 1278' having ATCC Accession Number PTA-126609.
2. A lettuce plant produced by growing the seed of claim 1.
3. A lettuce head isolated from the plant of claim 2.
4. A lettuce plant having all the physiological and morphological characteristics of the lettuce plant of claim 2.
5. A F1 hybrid lettuce plant having 'PRO 1278' as a parent where 'PRO 1278' is grown from the seed of claim 1.
6. Pollen of the plant of claim 2.
7. An ovule of the plant of claim 2.
8. Tissue culture of the plant of claim 2.
9. A method of selecting lettuce, comprising
   a. growing more than one plant from a plurality of seeds of claim 1; and
   b. selecting a plant grown from the plurality of seeds from step a).
10. A selected lettuce plant selected by the method of claim 9, step b).
11. A lettuce seed produced from the selected lettuce plant of claim 10.

* * * * *